(12) United States Patent
Ma et al.

(10) Patent No.: US 10,450,603 B2
(45) Date of Patent: Oct. 22, 2019

(54) FLUORESCENCE DETECTION DEVICE

(71) Applicant: Delta Electronics Int'l (Singapore) Pte Ltd, Singapore (SG)

(72) Inventors: Bo Ma, Singapore (SG); Wei-Chen Hsu, Singapore (SG); Jei-Yin Yiu, Singapore (SG)

(73) Assignee: DELTA ELECTRONICS INT'L (SINGAPORE) PTE LTD, Singapore (SG)

( * ) Notice: Subject to any disclaimer, the term of this patent is extended or adjusted under 35 U.S.C. 154(b) by 221 days.

(21) Appl. No.: 15/619,822

(22) Filed: Jun. 12, 2017

(65) Prior Publication Data
US 2018/0073054 A1  Mar. 15, 2018

Related U.S. Application Data

(60) Provisional application No. 62/393,275, filed on Sep. 12, 2016.

(30) Foreign Application Priority Data

May 26, 2017 (SG) .......................... 10201704313T

(51) Int. Cl.
*C12Q 1/686* (2018.01)
*B01L 7/00* (2006.01)
*G01N 21/64* (2006.01)

(52) U.S. Cl.
CPC ............ *C12Q 1/686* (2013.01); *B01L 7/52* (2013.01); *G01N 21/645* (2013.01);
(Continued)

(58) Field of Classification Search
CPC ............ G01N 21/6428; G01N 21/645; G01N 2021/6439; G01N 2021/6463; B01L 7/52;
(Continued)

(56) References Cited

U.S. PATENT DOCUMENTS 6,246,525 B1  6/2001 Ikami
6,498,690 B2  12/2002 Ramm et al.
(Continued)

FOREIGN PATENT DOCUMENTS

TW  M393517 U  12/2010
TW  201407150 A  2/2014

OTHER PUBLICATIONS

Hatch et al. "Continuous flow real-time PCR device using multi-channel fluorescence excitation and detection", The Royal Society of Chemistry, Lab Chip 2014, 14, pp. 562-568, (Year: 2014).*

*Primary Examiner* — David P Porta
*Assistant Examiner* — Meenakshi S Sahu
(74) *Attorney, Agent, or Firm* — Kirton McConkie; Evan R. Witt

(57) ABSTRACT

The fluorescence detection device includes an illumination module and a detection module. The illumination module includes a light source and a first filter. The light source is configured with the first filter to pass a first light beam at a first particular bandwidth along a first optical axis for exciting a targeted fluorescent probe and generating a fluorescent light. The detection module includes a second filter and a photo-detector. The second filter receives the fluorescent light and passes a second light beam at a second particular bandwidth along a second optical axis. The photo-detector receives the second light beam at the second particular bandwidth and converts the second light beam at the second particular bandwidth to an electrical signal. The first optical axis is tilted from the second optical axis at a specific angle ranged from 4.5 degrees to 9.5 degrees.

20 Claims, 22 Drawing Sheets

(52) U.S. Cl.
CPC .. *G01N 21/6428* (2013.01); *B01L 2300/0654* (2013.01); *B01L 2300/1822* (2013.01); *G01N 2021/6439* (2013.01); *G01N 2021/6463* (2013.01)

(58) Field of Classification Search
CPC ..... B01L 2300/1822; B01L 2300/0654; C12Q 1/686
USPC ....................................................... 250/461.1
See application file for complete search history.

(56) References Cited

U.S. PATENT DOCUMENTS

| | | | |
|---|---|---|---|
| 6,746,864 B1 | 6/2004 | Karlton et al. | |
| 6,852,986 B1 | 2/2005 | Lee et al. | |
| 6,940,598 B2 * | 9/2005 | Christel ............... | B01J 19/0093 250/458.1 |
| 6,982,166 B2 | 1/2006 | Sandell | |
| 7,015,484 B2 | 3/2006 | Gillispie et al. | |
| 7,148,043 B2 | 12/2006 | Kordunsky et al. | |
| 7,273,749 B1 | 9/2007 | Wittwer et al. | |
| 7,289,217 B2 | 10/2007 | Boege et al. | |
| 7,315,376 B2 | 1/2008 | Bickmore, Jr. et al. | |
| 7,369,227 B2 | 5/2008 | Gutekunst et al. | |
| 7,370,994 B2 | 5/2008 | Li | |
| 7,663,750 B2 | 2/2010 | Bahatt et al. | |
| 7,687,260 B2 | 3/2010 | Gutekunst | |
| 7,700,928 B2 | 4/2010 | Rasnow et al. | |
| 7,749,736 B2 | 7/2010 | Kordunsky et al. | |
| 8,029,733 B2 | 10/2011 | Chang et al. | |
| 8,278,114 B2 | 10/2012 | Gambini et al. | |
| 8,441,629 B2 | 5/2013 | Kolesnychenko et al. | |
| 8,557,569 B2 | 10/2013 | Boege et al. | |
| 8,865,473 B2 | 10/2014 | Gambini et al. | |
| 8,900,828 B2 | 12/2014 | Smith et al. | |
| 8,921,098 B2 | 12/2014 | Gambini et al. | |
| 8,987,685 B2 | 3/2015 | Fawcett et al. | |
| 9,080,207 B2 | 7/2015 | Handique et al. | |
| 9,096,892 B1 | 8/2015 | Klemer et al. | |
| 2001/0046050 A1 | 11/2001 | Hoyt | |
| 2003/0011772 A1 | 1/2003 | Abe et al. | |
| 2004/0178357 A1 | 9/2004 | King | |
| 2005/0133724 A1 | 6/2005 | Hsieh et al. | |
| 2006/0289786 A1 | 12/2006 | Taylor et al. | |
| 2007/0114444 A1 | 5/2007 | Reid et al. | |
| 2008/0277595 A1 | 11/2008 | Lundquist et al. | |
| 2009/0009767 A1 | 1/2009 | Boege et al. | |
| 2010/0227386 A1 * | 9/2010 | Neuzil ..................... | B01L 7/52 435/288.7 |
| 2014/0273181 A1 | 9/2014 | Abbott et al. | |
| 2014/0283945 A1 | 9/2014 | Jones et al. | |
| 2015/0007327 A1 | 1/2015 | Morris et al. | |
| 2015/0073273 A1 | 3/2015 | Unno et al. | |
| 2015/0232916 A1 | 8/2015 | Rasmussen et al. | |

* cited by examiner

FLUORESCENCE DETECTION DEVICE

CROSS-REFERENCE TO RELATED APPLICATION

This application claims the benefit of U.S. Provisional Application Ser. No. 62/393,275 filed on Sep. 12, 2016, and claims the priority to Singapore Patent Application No. 10201704313T filed on May 26, 2017, the entire contents of which are incorporated herein by reference for all purposes.

FIELD OF THE INVENTION

The present invention relates to a fluorescence detection device, and more particularly to a fluorescence detection device with high signal-to-noise ratio.

BACKGROUND OF THE INVENTION

The demand of acquiring large amounts of a specific segment of DNA efficiently for different purposes is booming in recent years. Among the entire existing DNA sequencing techniques, Polymerase Chain Reactions (PCR) is one of the most economical and straightforward techniques amplifying billion copies of targeted DNA segments in short period of time. The applications of PCR technique are broadly adopted, such as selective DNA isolation for genetic identification, forensic analysis for analyzing ancient DNA in archeology, medical applications for genetic testing and tissue typing, fast and specific diagnosis of infectious diseases for hospitals and research institutes, inspection of environmental hazards for food safety, genetic fingerprint for investigating criminals, and so on. For PCR technique, only small amount of DNA samples are required from blood or tissues. By utilizing fluorescent dye into the nucleic acids solutions, the amplified DNA segments could be detected through the help of fluorescent molecules.

To simultaneously detect and analyze the presence of targeted nucleic acids in a batch of biological samples, fluorescent dyes detection technique is usually applied. After the light source at specific wavelength illuminates on the targeted nucleic acids, the DNA-binding dyes or fluorescein-binding probes of the nucleic acids will react and enable fluorescent signals to be emitted. The fluorescent signal is an indication of the existence of the targeted nucleic acids. This technique has been employed for the novel PCR technique, which is called real time quantitative PCR or qPCR. qPCR is the early-phase PCR detection with higher sensitivity and better precision than the conventional PCR technique which is an end-point PCR detection. An optical device is essential to detect the fluorescent light emitted from the specific nucleic acids segments for qPCR technique. The optical device has to provide a light source to excite fluorescent probes at their specific wavelengths, and in the meanwhile, it detects the fluorescent signals emitted from the probes.

The fluorescent detection systems have been well developed in many fields, such as the application of fluorescence spectroscopy and fluorescence microscopy. An array of single color light source with a set of filters and optical components could easily apply on particular fluorescent probe. However, the difficulties of developing a fluorescence detection device for portable qPCR system have not been solved in the market because of its cost and size with high signal-to-noise ratio (SNR).

In light with the requirements and the issues addressed above, there is a need of providing an improved fluorescence detection device with high signal-to-noise ratio for qPCR application.

SUMMARY OF THE INVENTION

An object of the present invention is to provide a fluorescence detection device with high signal-to-noise ratio for minimizing the size and the weight of the device, and still providing superior performance for a portable qPCR system with affordable cost.

According to an aspect of the present invention, there is a fluorescence detection device including an illumination module and a detection module. The illumination module includes at least one light source and at least one first filter. The light source provides a broadband illumination and is configured with the first filter to pass a first light beam at a first particular bandwidth along a first optical axis for exciting a targeted fluorescent probe of a fluorescent reaction mixture stored in a tube and generating a fluorescent light. The detection module includes at least one second filter and at least one photo-detector. The second filter receives the fluorescent light and passes a second light beam at a second particular bandwidth along a second optical axis. The photo-detector receives the second light beam at the second particular bandwidth and converts the second light beam at the second particular bandwidth to an electrical signal. The first optical axis is tilted from the second optical axis at an angle ranged from 4.5 degrees to 9.5 degrees.

In an embodiment, the light source is one selected from a group consisted of a single color LED, a laser diode, a mercury lamp and a halogen light bulb.

In an embodiment, the first filter and the second filter are single band pass filters.

In an embodiment, the first filter and the second filter are an excitation filter and an emission filter respectively In an embodiment, the fluorescence detection device further includes a heating module disposed between the illumination module and the detecting module, wherein the heating module includes at least one heating chamber adapted for accommodating the tube having the fluorescent reaction mixture and the targeted fluorescent probe.

In an embodiment, the heating module further comprises a heater connected with the heating chamber.

In an embodiment, the heater is a thermoelectric cooling heater for thermal cycling control.

In an embodiment, the heating module further includes at least one first optical aperture and at least one second optical aperture, the first optical aperture is located at the first optical axis, the second optical aperture is located at the second optical axis, and the first optical aperture is communicated with the second optical aperture through the heating chamber.

In an embodiment, the diameter of the first optical aperture is ranged from 1.8 mm to 2.2 mm, and the diameter of the second optical aperture is ranged from 1.5 mm to 2.5 mm.

In an embodiment, the illumination module further includes at least one pine hole located between the first filter and the first optical aperture and centered on the first optical axis, and the diameter of the pin hole is ranged from 1.3 mm to 1.8 mm.

In an embodiment, the second optical aperture of the heating module and the detection module are configured together to form a divergent half angle ranged from 18 degrees to 22 degrees.

In an embodiment, the detection module further comprises at least one condensing optic disposed between the tube and the second filter.

In an embodiment, the condensing optic includes a plano surface facing to the second optical aperture and a convex surface facing to the second filter.

In an embodiment, the detection module further comprises at least one imaging optic mounted between the second filter and the photo-detector.

In an embodiment, the imaging optic includes a plano surface facing to the photo-detector and a convex surface facing to the second filter.

In an embodiment, the detection module further comprises at least two optics symmetrically disposed in two opposite sides of the second filter with a same distance, wherein the convex surface of each optic faces toward the second filter.

In an embodiment, the fluorescence detection device includes a housing, wherein the illumination module and the detection module are constructed together on the housing.

In an embodiment, the detection module further comprises an electromagnetic shielding and grounding structure covering the photo-detector.

In an embodiment, the photo-detector is one selected from a group consisted of a silicon photodiode, a photomultiplier tube, a charged-couple device, and a complementary metal-oxide semiconductor.

The above objects and advantages of the present invention become more readily apparent to those ordinarily skilled in the art after reviewing the following detailed description and accompanying drawings, in which:

DETAILED DESCRIPTION OF THE PREFERRED EMBODIMENT

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

The present invention provides a fluorescence detection device which is an optical module sequentially illuminating multiple fluorescent samples arranged in linear position. During the qPCR amplification process, the fluorescence detection device provides a single light source to excite fluorescent probes in the nucleic acid sample, and sequentially detects specific fluorescent signals emitted from the probes.

Figure 1:
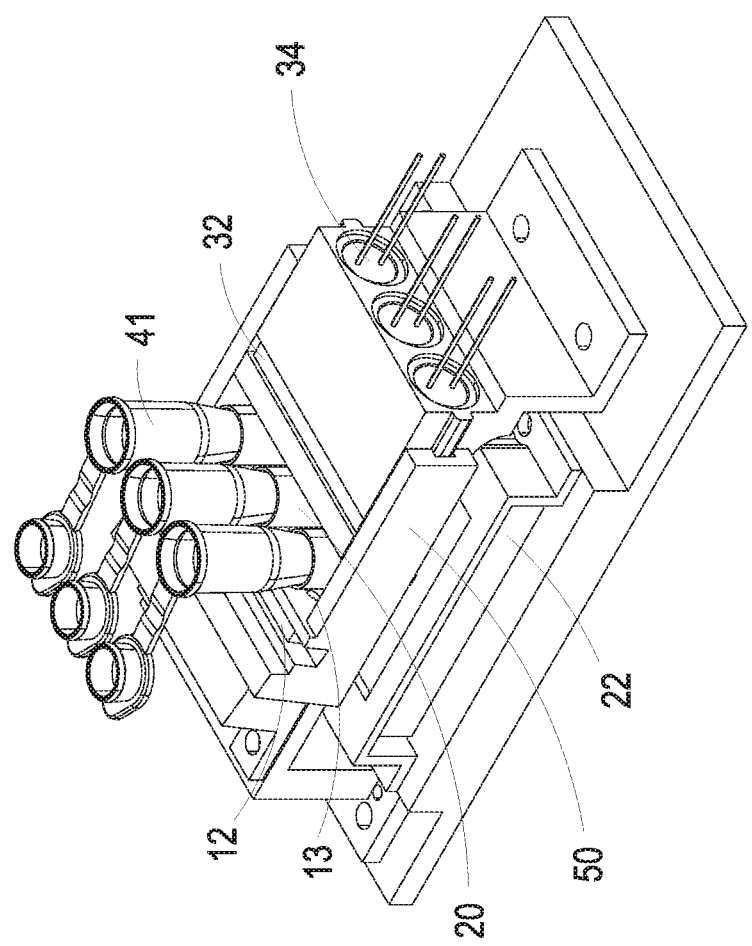
FIG. 1 shows a schematic view of the fluorescence detection device according to a preferred embodiment of the present invention.
Figure 2:
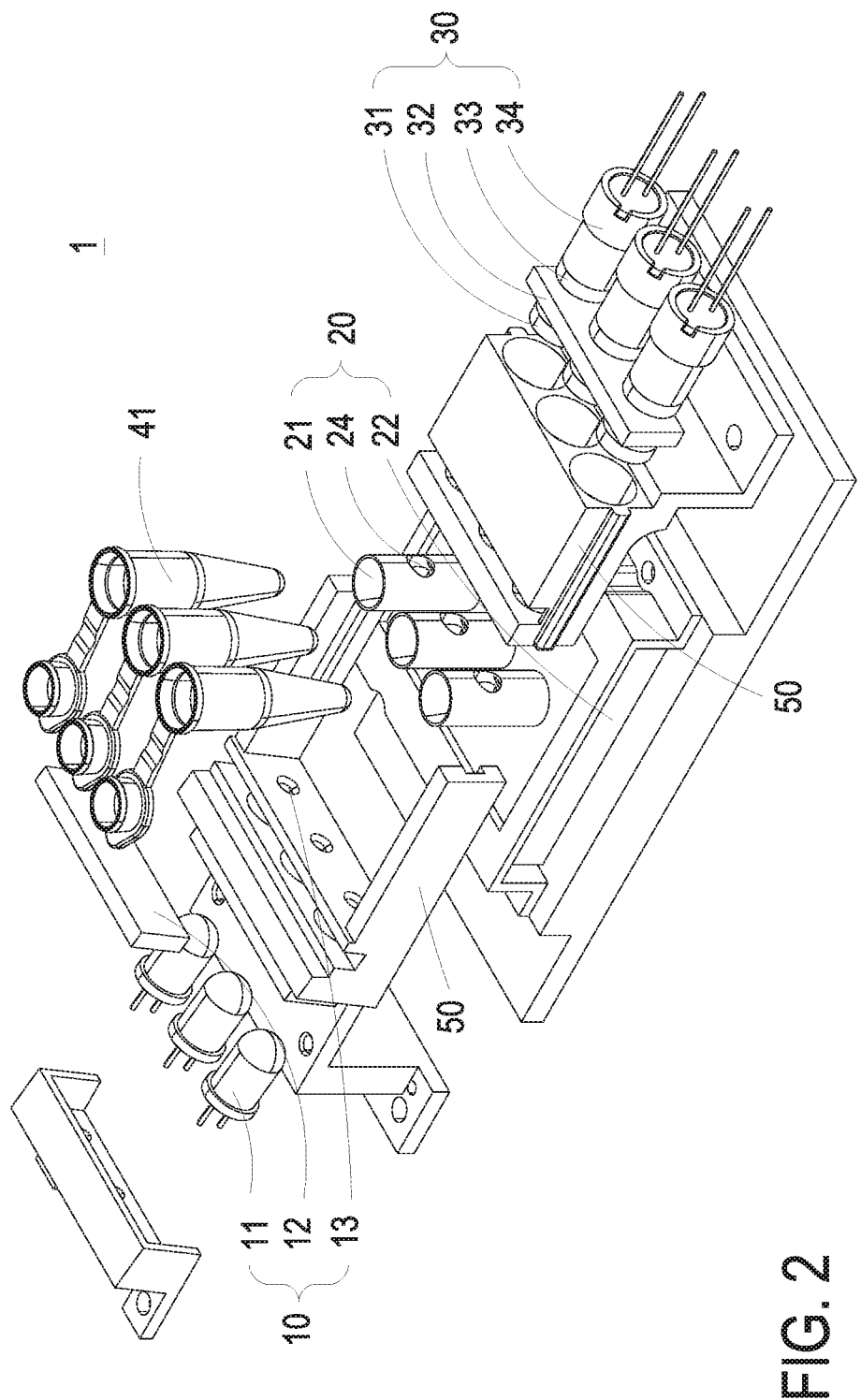
FIG. 2 shows an exploded view of the fluorescence detection device of FIG. 1.
Figure 3:
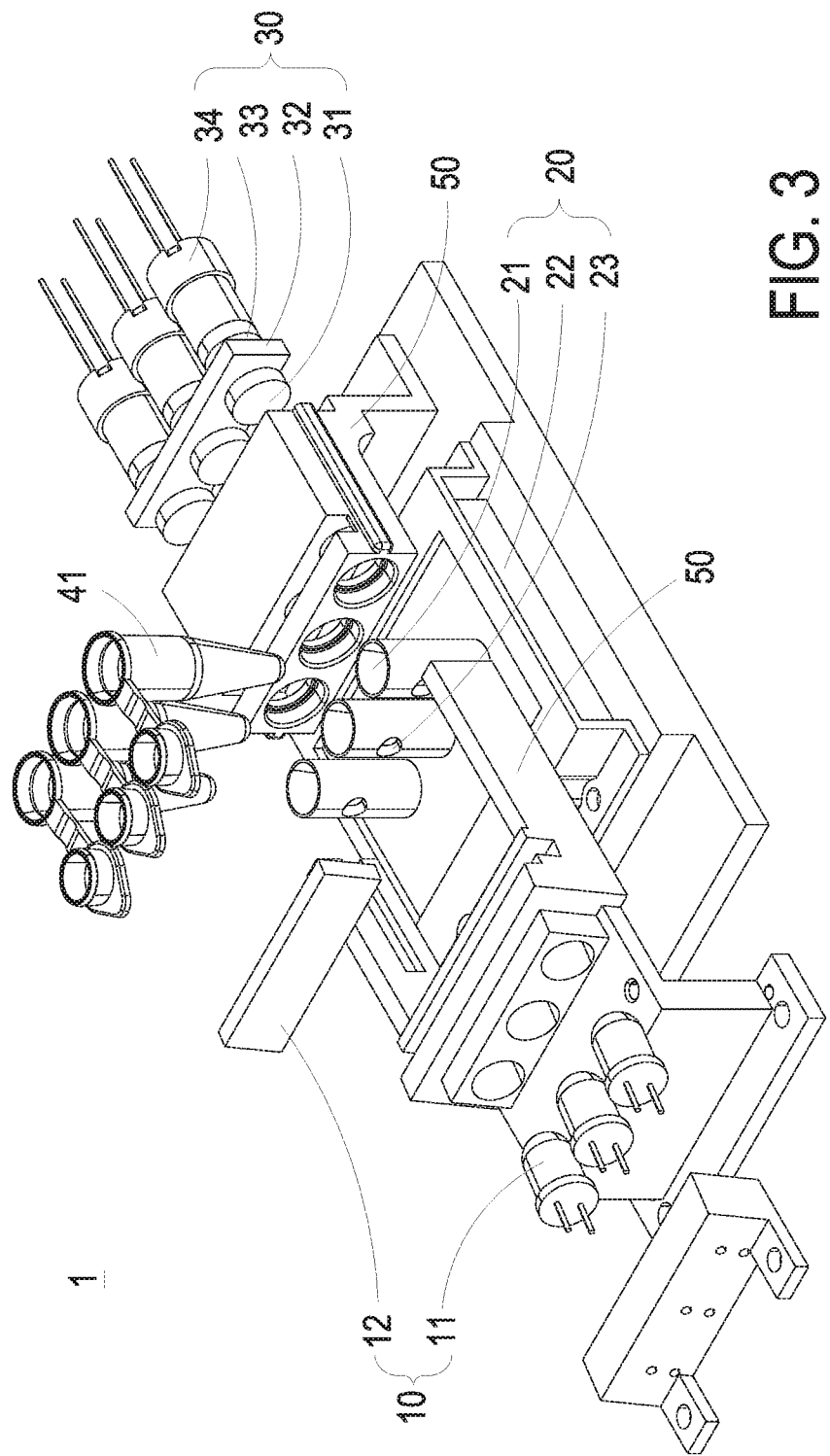
FIG. 3 shows another exploded view of the fluorescence detection device of FIG. 1 from a different orientation.
Figure 4:
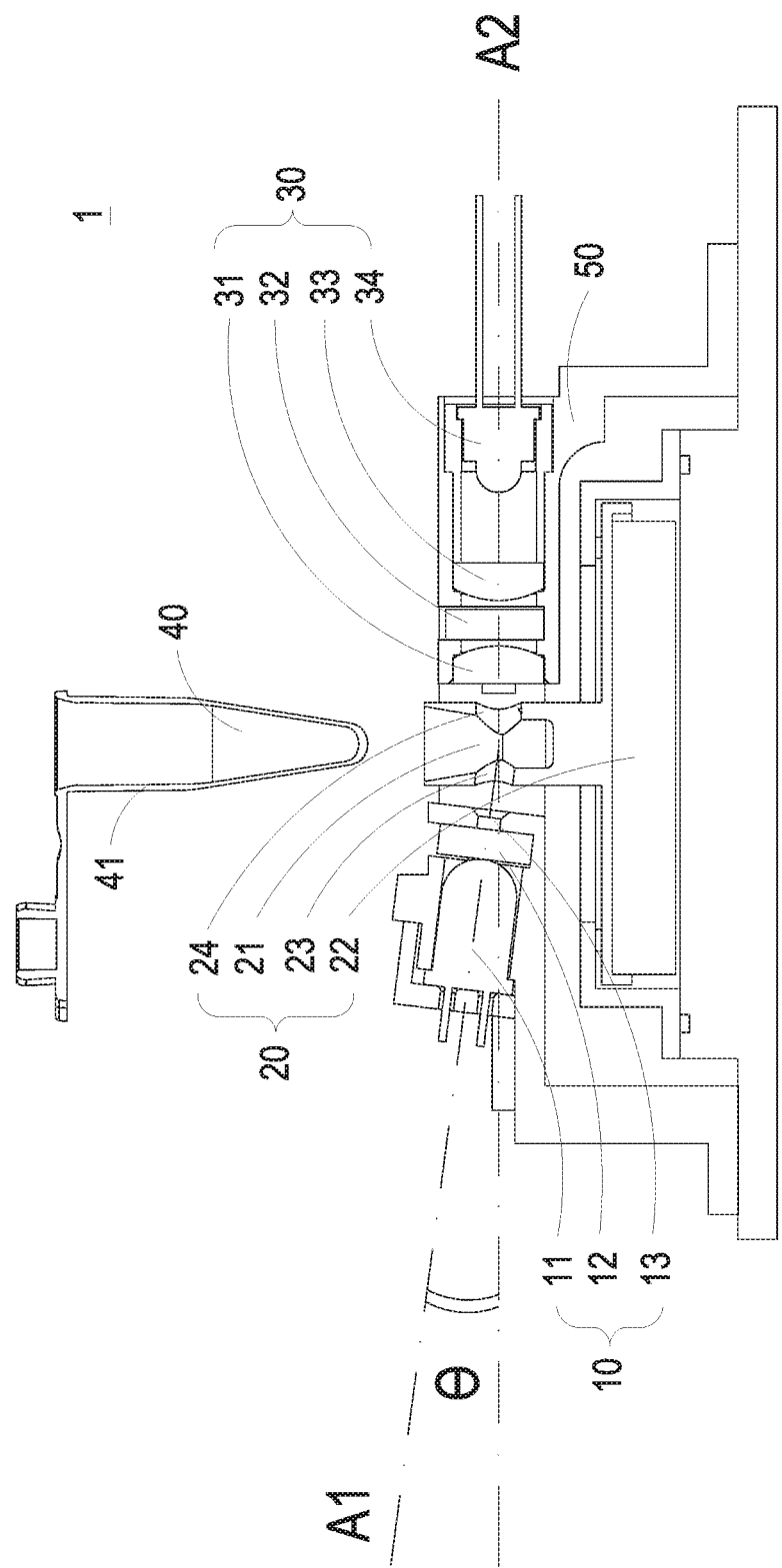
FIG. 4 shows a cross-sectional view of the fluorescence detection device of FIG. 1.

Please refer to FIGS. 1 to 4, wherein FIG. 1 shows a schematic view of the fluorescence detection device according to a preferred embodiment of the present invention, FIGS. 2 to 3 show exploded views of the fluorescence detection device of FIG. 1 from different orientations, respectively, and FIG. 4 shows a cross-sectional view of the fluorescence detection device of FIG. 1. As shown in FIGS. 1 to 4, the present invention provides the fluorescence detection device 1 including an illumination module 10 and a detection module 30. The illumination module 10 includes a light source 11 and a first filter, such as a first single band pass filter 12. The light source 11 is configured with the first single band pass filter 12 to pass a first light beam at a first particular bandwidth along a first optical axis A1 for exciting a targeted fluorescent probe of a fluorescent reaction mixture 40 stored in a tube 41 and generating a fluorescent light. The detection module 30 includes a second filter, such as a second signal band pass filter 32, and a photo-detector 34. The second signal band pass filter 32 receives the fluorescent light and passes a second light beam at a second particular bandwidth along a second optical axis A2. The photo-detector 34 receives the second light beam at the second particular bandwidth and converts the second light beam at the second particular bandwidth to an electrical signal. The first optical axis A1 is tilted from the second optical axis A2 at a specific angle ranged from 4.5 degrees to 9.5 degrees. Furthermore, the fluorescence detection device 1 further includes a heating module 20 disposed between the illumination module 10 and the detecting module 30 for accommodating a tube having a fluorescent reaction mixture and the targeted fluorescent probe and maintaining the thermal cycling control thereof. Namely, the fluorescence detection device 1 mainly includes an illumination module 10, a heating module 20, and a detection module 30. The illumination module 10 is located in front of the heating module 20, and the detection module 30 is located behind the heating module 20. The illumination module 10, the heating module 20 and the detection module 30 are constructed together on a housing 50.

In the embodiment, the illumination module 10 includes at least one light source 11, and at least one first filter, such as the first single band pass filter 12. The light source 11 provides a broadband illumination and the wavelength of the light source 11 includes the excitation bandwidth for exciting a targeted fluorescent probe of a fluorescent reaction mixture (also called as PCR mixture) 40 stored in a PCR tube 41. The illumination module 10 is configured on a first optical axis A1 designed to tilt a specific angle θ ranged from 4.5 degrees to 9.5 degrees downward relative to a second optical axis A2 of the detection module 30. Preferably, the specific angle θ ranged from 4.5 degrees to 9.5 degrees. In the embodiment, a light emitting diode (LED) is chosen as the light source 11, but other light sources, such as but not limited to laser diode and halogen light bulb, could also be applied. The first single band pass filter 12 applied in the illumination module 10 is an excitation filter and only allows the light falling within excitation bandwidth to pass through and reach the PCR mixture 40. Namely, the first single band pass filter 12 provides an excitation light signal for the targeted fluorescent probe. The bandwidth of the first single band pass filter 12 is ranged from 20 nm to 30 nm.

Moreover, in the embodiment, as shown in FIGS. 1 to 4, the illumination module 10 includes three channels positioned linearly and constructed on the housing 50, but the number of channels is expandable for the requirement of batching processing in large volume. Each channel has its own light source 11, and a pin hole 13 ranged from 1.3 mm to 1.8 mm in diameter of each channel is required to prevent the excitation light beam at large angle causing scattered light, which is one of the sources of background noise. The material of the housing 50 is black acrylonitrile butadiene styrene (ABS) for its low thermal conductivity, high thermal resistivity, and reduction of internal light scattering. Other kinds of black plastic materials with low reflectivity, or aluminum coated by black anodized coating possessing low reflectance and high absorptance are also applicable.

Figure 5:
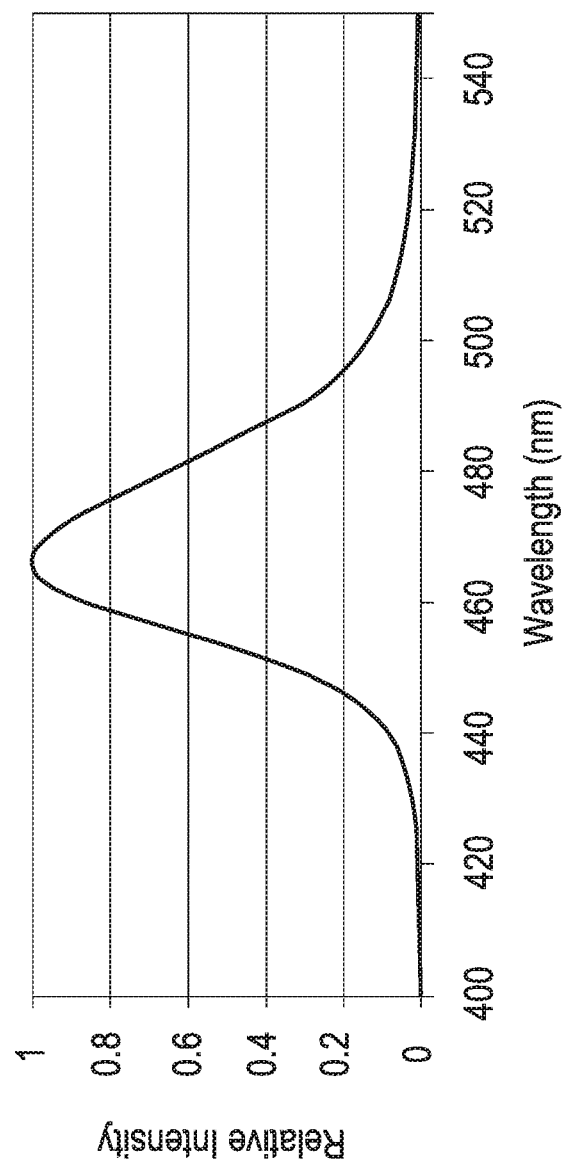
FIG. 5 shows a spectrum of the light source according to a preferred embodiment of the present invention.

FIG. 5 shows a spectrum of the light source according to a preferred embodiment of the present invention. In the embodiment, the light source 11 emits light within a particular range of wavelengths in visible wavelengths, e.g. between 450.34 nm to 481.26 nm at full-width at half maximum (FWHM) covering targeted excitation wavelengths. Preferably, the light source 11 is a single-color LED light source providing optical power in 7000 mcd at 20 mA, and its viewing angle at FWHM is 20 degrees. Moreover, any kind of light source 11 whose spectra include the excitation spectra of fluorescent dyes, such as a laser, mercury lamps, halogen lamps, etc. are applicable.

Figure 6:
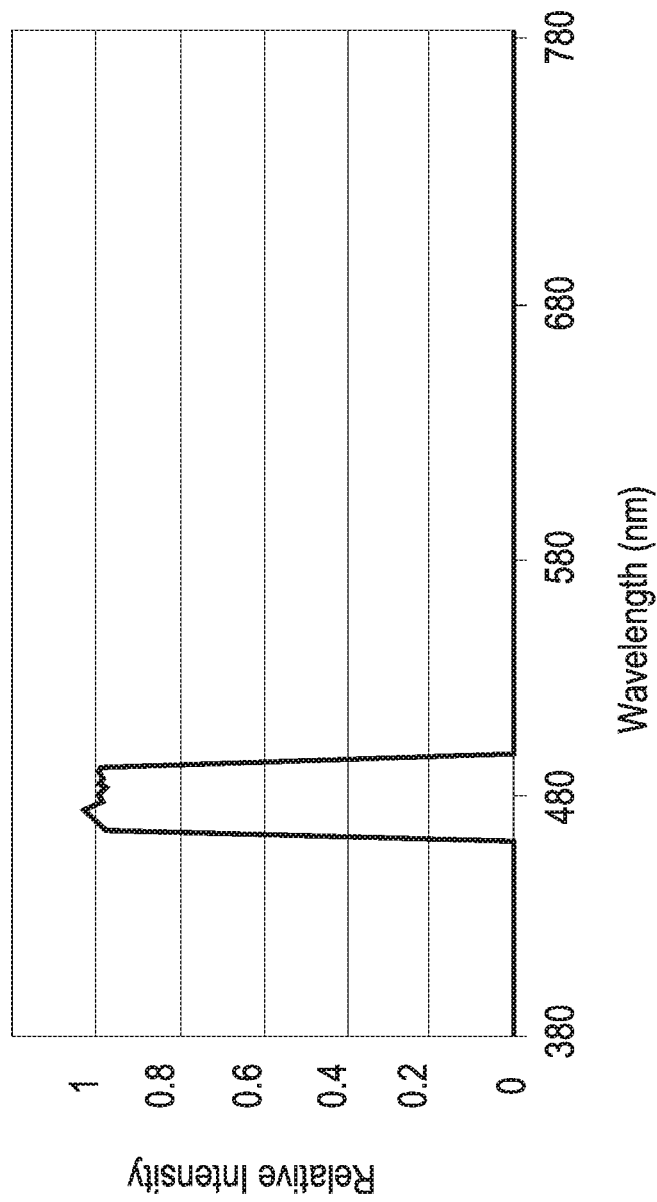
FIG. 6 shows the pass band of the first single band pass filter according to a preferred embodiment of the present invention.
Figure 7:
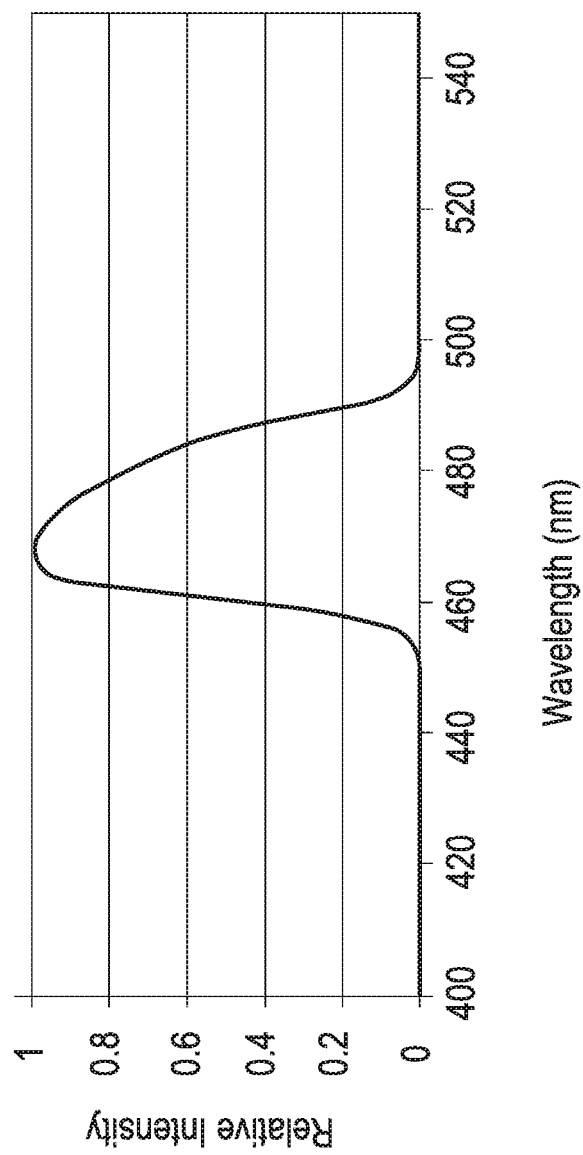
FIG. 7 shows a spectra of the light source with the first single band pass filter according to a preferred embodiment of the present invention.

On the other hand, FIG. 6 shows the pass band of the first single band pass filter according to a preferred embodiment of the present invention, and FIG. 7 shows a spectra of the light source with the first single band pass filter according to a preferred embodiment of the present invention. In the embodiment, the first single band pass filter 12 is an optical component that is capable of passing a specific wavelength for excitation from the light source 11, and yet blocking the rest portions of the wavelengths as noise signal. Namely, the light source 11 is configured with the first single band pass filter 12 to pass a first light beam at a first particular bandwidth along the first optical axis A1 for exciting the targeted fluorescent probe of the fluorescent reaction mixture 40 stored in the PCR tube 41 and generating a fluorescent light. In the embodiment, the pass band of the first single band pass filter 12 is about 27 nm. The passed wavelength is ranged from 460.5 nm to 487.5 nm. So the first single band pass filter 12 could help to increase the signal to noise ratio (SNR) of the targeted excitation fluorescent dye. In the embodiment, the dimension of the first single band pass filter 12 is 23 mm×6.5 mm×2 mm to cover three channels. In another embodiment, the dimension of the first single band pass filter 12 could be broken into 5 mm×5 mm×2 mm for each channel for further cost down.

Figure 8:
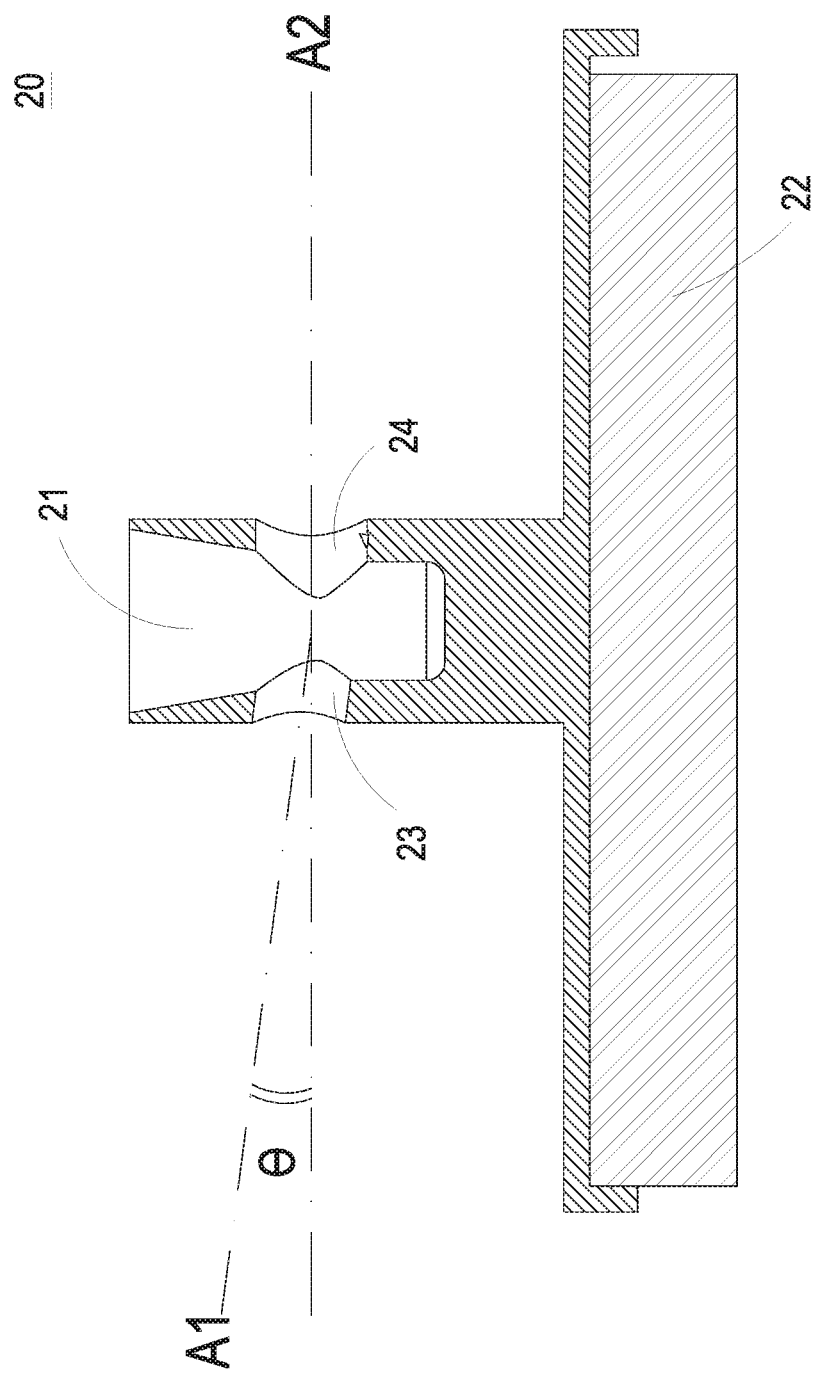
FIG. 8 shows a cross sectional view of the heating module of FIG. 1.

FIG. 8 shows a cross sectional view of the heating module of FIG. 1. As shown in FIGS. 1 to 4 and 6, the heating module 20 includes a heating chamber 21, a heater 22, a first optical aperture 23 and a second optical aperture 24. The heating module 20 could accommodate multi-channels laterally to achieve multiplexing sample detection. The material of the heating chamber 21 chosen in the embodiment is copper, which is thermally conductive, and transfers heat uniformly in minutes to meet rapid thermal cycling requirement. Other thermally conductive material might be applied, such as aluminum. In the embodiment, a thermoelectric cooling (TEC) heater is chosen as the heater 22, and the heating chamber 21 is mounted on top of the heater 22. Moreover, the first optical aperture 23 and the second optical aperture 24 created at the front and the rear of the heating chamber 21 enable the efficient light signal transmission input from light source 11 and emitted from the PCR mixture 40, respectively. The heater 22 changes temperature in cycle followed by the variation of input current.

Figure 9:
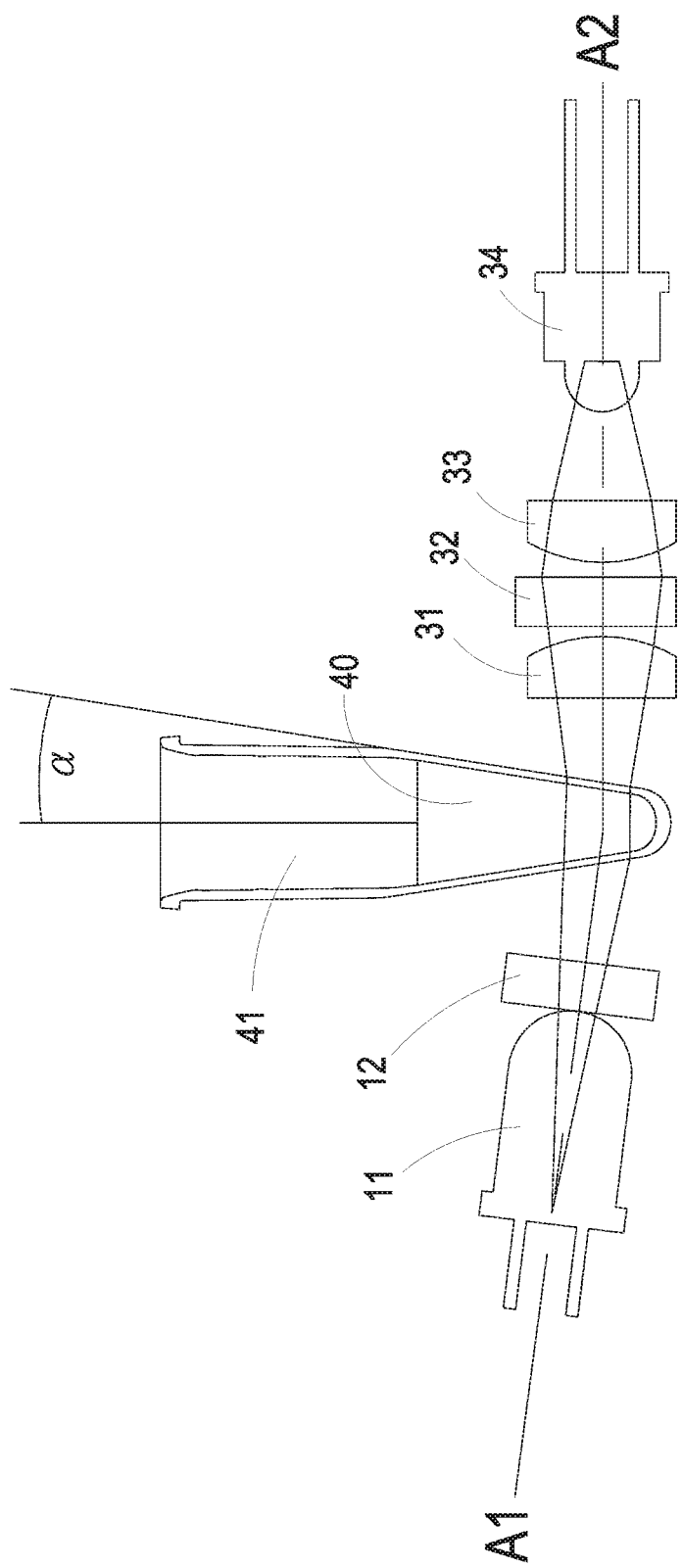
FIG. 9 shows the light path of the fluorescence detection device in one channel according to a preferred embodiment of the present invention.

FIG. 9 shows the light path of the fluorescence detection device in one channel according to a preferred embodiment of the present invention. In the embodiment, bio-samples are prepared and restored in PCR tube 41 for PCR amplification and detection. As shown in FIGS. 4 and 9, the first optical aperture 23 and the second optical aperture 24 are created on the front and rear sides of PCR heating chamber 21. Namely, the first optical aperture 23 is communicated with the second optical aperture 24 through the heating chamber 23. The diameter of the first optical aperture 23 is ranged from 1.8 mm to 2.2 mm and located at the first optical axis A1. The first optical axis A1 is tilted clockwise from the second optical axis A2 at a specific angle ranged from 4.5 degrees to 9.5 degrees so as to detect maximum fluorescent emission signal. Besides, the diameter of the second optical aperture 24 is ranged from 1.5 mm to 2.5 mm and located at the second optical axis A2.

When excitation light beam transmits through the fluorescent reaction mixture 40 with the targeted fluorescent probe stored in the PCR tube 41, due to the shape of the PCR tube 41, and the refractive index of the tube material, which is ranged from 1.46 to 1.49, and the refractive index of the fluorescent reaction mixture 40 with the targeted fluorescent probe is also higher than the air, the incident angle of light beam is designed to provide maximum intensity for excitation.

Moreover, as shown in FIGS. 1 to 4, for holding and heating the PCR tube 41, the heating chamber 21 is made of copper for its superior thermal conductivity. Certainly, other thermally conductive material might be applied, such as aluminum. Each heating chamber 21 is positioned linearly for the batch process. Moreover, the heating chamber 21 could be made from metals and other materials with high thermal conductivity, and it could be fabricated by computer numerical control machining (CNC) machining, casting, laser-cutting, 3D printing, etc. The PCR tube 41 includes a volume inside ranged from 30 μL to 40 μL. In the embodiment, the heater 22 is a thermoelectric cooling (TEC) heater. Temperature control of the heater 22 could be within a fraction of degree, so the requirement of cyclic PCR amplification could be fulfilled. Comparing to other thermal cycler, the compactness of TEC heater contributes the miniaturization of the system. Furthermore, the TEC heater has long life time, and is easy to maintain. Certainly, other than TEC technology, convectional thermal cycling methods through air or liquid are applicable.

On the other hand, in the embodiment, the fluorescence detection device 1 further includes the detection module 30 for detecting specific fluorescent signals emitted from the fluorescent reaction mixtures 40 with the targeted fluorescent probe. The sandwich structure of detection module 30 includes a condensing optic 31, a second single band pass filter 32, an imaging optic 33 and a photo-detector 34. The second single band pass filter 32 can be an emission filter, and the photo-detector 34 can be a photodiode. The number of detection channels of the detection module 30 is the same as that of the light sources 11. Each channel of the illumination module 10 maps the detection channel of detection module 30.

As shown in FIG. 4, the detection module 30 designed in a sandwich type structure includes a group of condensing optics 31, at least one piece of second single band pass filter 32, a group of imaging optics 33, and at least one photo-detector 34. The condensing optic 31 sits behind the second optical aperture 24 of the heating module 20. The condensing optic 31 collects the fluorescent emitting signal from the PCR mixture 40, and ensures the collimating beam entering into the second single band pass filter 32. The second single band pass filter 32 locating behind the condensing optics 31 only enables the fluorescent emission signal falling within its pass band to transmit. The bandwidth of the second band pass filter 32 is ranged from 20 nm to 30 nm. In the embodiment, the imaging optics 33 focuses the filtered emission signal on the photo-detector 34 to provide sufficient fluorescent emission signal for analysis. The photo-detector 34 converts the fluorescent emission signal to electrical signal for further analysis. In the embodiment, a photodiode can be chosen as the photo-detector 34, but other types of detector, such as a CCD, a PMT, and a CMOS could work on the fluorescence detection device 1 as well. The materials of the condensing optic 31 and the imaging optic 33 applied in this invention are optical grade glass, but injection molded optical plastic, such as acrylic (PMMA), polycarbonate (PC), polystyrene or polyolefin, are also applicable.

Figure 10A:
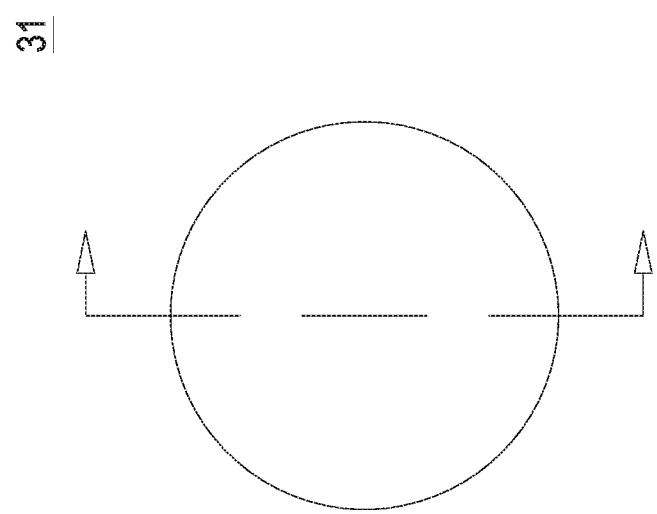
FIGS. 10A and 10B show a front view and a cross-sectional view of the condensing optic according to a preferred embodiment, respectively.
Figure 10B:
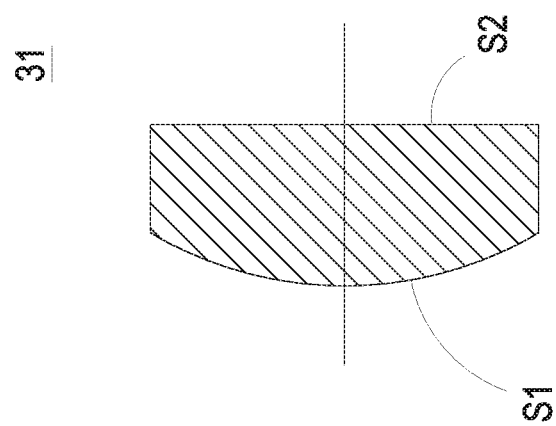

In the embodiment, the condensing optic 31 positioned behind the heating chamber 21 is for collecting fluorescent light emitted from the fluorescent reaction mixtures 40 with the targeted fluorescent probe stored in PCR tube 41. FIGS. 10A and 10B show a front view and a cross-sectional view of the condensing optic according to a preferred embodiment, respectively. The condensing optic 31 includes a convex surface S1 and a plano surface S2. The radius of curvature of the condensing optic 31 is 5.89 mm. The plano surface S2 faces the heating chamber 21 and the convex surface S1 faces the second single band pass filter 32. The condensing optic 31 is utilized to collect the fluorescent light, and transform the fluorescent light to a collimating beam to evenly illuminate on the second single band pass filter 32. The second single band pass filter 32 (23 mm×6.2 mm×2 mm) covers all three channels. However, the sizes of the second single band pass filter 32 could be reduced to 5 mm×5 mm×2 mm for further cost down. The material of the condensing optic 31 is N-SF11, and other materials, such as BK7 glass, optical grade plastic fabricated by injection molds, such as acrylic (PMMA), polycarbonate (PC), polystyrene, or polyolefin are all applicable. The numerical aperture (NA) value of the condensing optic 31 is ranged from 0.37 to 0.42.

Figure 11:
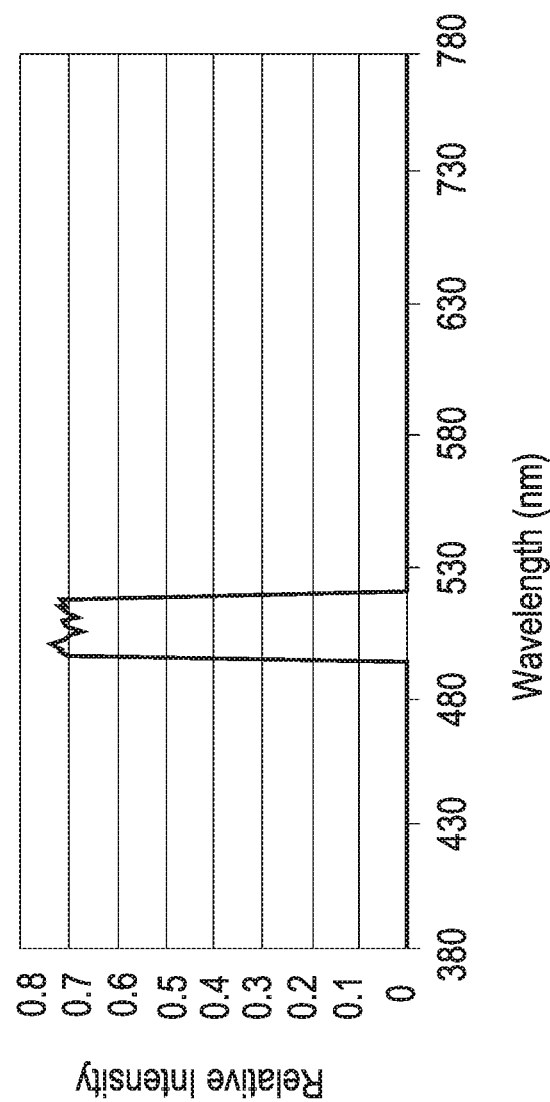
FIG. 11 shows the pass band of the second single band pass filter according to a preferred embodiment of the present invention.

It is noted that each channel requires a first filter as the excitation filter and a second filter as the emission filter. In the embodiment, each channel includes one piece of the first single band pass filter 12 and one piece of the second single band pass filter 32 to be constructed as the excitation filter and the emission filter, respectively. FIG. 11 shows the pass band of the second single band pass filter according to a preferred embodiment of the present invention. The emission wavelength of the targeted fluorescent probe is always longer than its excitation wavelength, so different filters are required. Similar to the first single band pass filter 12, the band pass coating of the second single band pass filter 32 only allows second light beam at particular wavelength to go through, and the rest portions of light will be blocked. The second single band pass filter 32 plays an important role for preventing the interference of noise signals from the light source 11 and stray lights from ambient environment. As shown in FIG. 11, the pass band of the second single band pass filter 32 is about 24 nm to filter out noise signals falling outside the pass band. The passed wavelength of the second single band pass filter 32 is from 512 nm to 536 nm.

Figure 12:
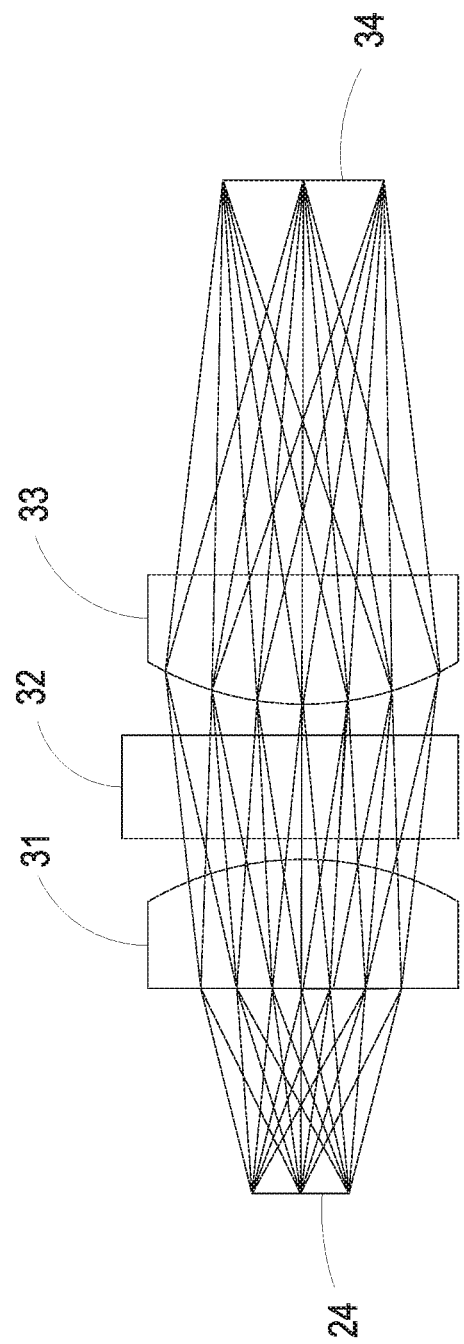
FIG. 12 shows the light path of the detection module according to a preferred embodiment of the present invention.

FIG. 12 shows the light path of the detection module according to a preferred embodiment of the present invention. In the embodiment, the imaging optic 33 is made of N-SF11 glass, and its whose configuration is the same as that of the condensing optic 31. The material of the imaging optic 33 is N-SF11, and other materials, such as BK7 glass, optical grade plastic fabricated by injection molds, such as acrylic (PMMA), polycarbonate (PC), polystyrene or polyolefin are all applicable. The numerical aperture (NA) value of the imaging optic 33 is ranged from 0.37 to 0.42. The imaging optic 33 sits behind the second single band pass filter 32 in the same distance away the second single band pass filter 32 as the condensing optic 31 to image filtered fluorescent signal at the image plane which is said the sensing surface of photo-detector 34. The convex surface of the imaging optic 33 faces toward the second single band pass filter 32. The symmetrical arrangement of the condensing optic 31 and the corresponding imaging optic 33, whose convex surfaces face to face, helps to reduce the wavefront aberration. The noise reflecting internally in the channel of the housing 50 (as shown in FIG. 4) is because the scattering light at large incident angle could transmit through band pass coating of the second single band pass filter 32. The imaging optic 33 converges the filtered emission fluorescent light which is uniformly distributed on a large area, and focuses it on the sensing surface of photo-detector 34 whose area (1.1 mm×1.1 mm) is much smaller than the fluorescent light source. The imaging optic 33 could accept the fluorescent signal from the PCR mixture 40 passing through the second optical aperture 24 of the heating chamber 21 within 18-22 degrees divergent angle (half angle).

Figure 13:
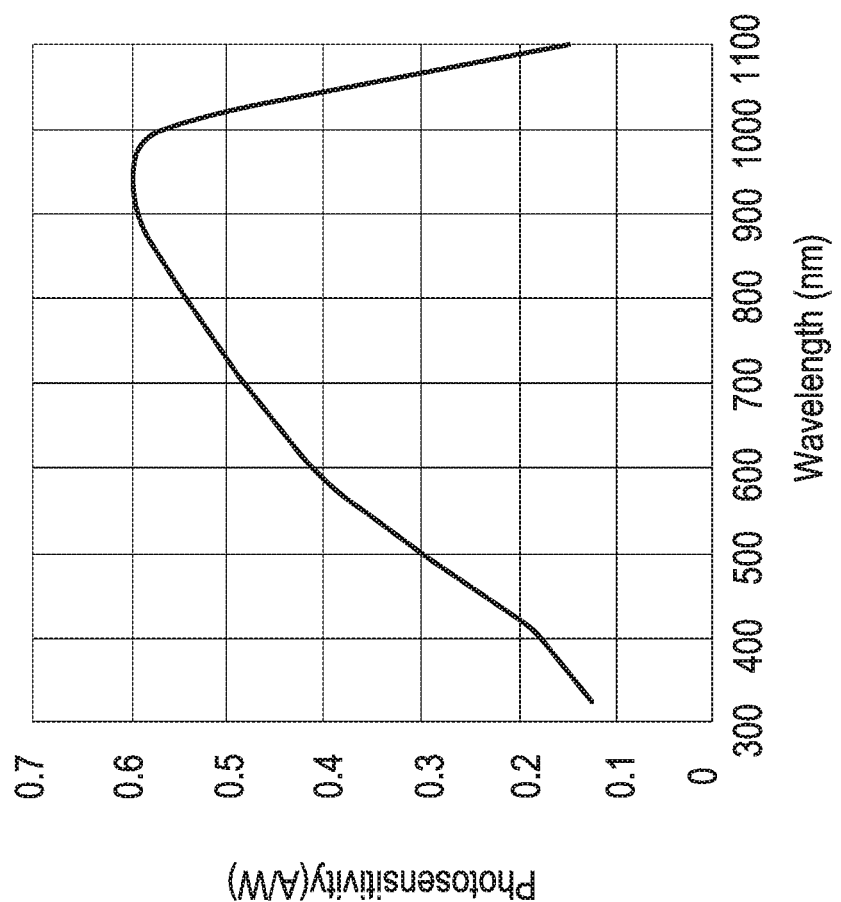
FIG. 13 shows the spectral response of a silicon photodiode.

In the embodiment, a silicon photodiode can be utilized as the photo-detector 34 to convert the photo signals to electrical current, and because of its high sensitivity, small numbers of photons of filtered fluorescent light could still be detected in the wavelength ranging from 320 nm to 1100 nm. FIG. 13 shows the spectral response of a silicon photodiode. Certainly, other types of photo-detectors, such as a photo-multiplier tube (PMT), a charged-couple device (CCD), and a complementary metal-oxide semiconductor (CMOS) are all applicable.

In an embodiment, the detection module 30 further includes a photodiode amplifier (not shown) required to convert electrical current output from the photo-detector 34 in few nano ampere to voltage. The photodiode amplifier amplifies the signal for further data analysis and utilization. The distance between the sensing surface of photo-detector 34 and the rear surface of imaging optic 33 is about 7 mm.

In an embodiment, the detection module 30 further includes the electromagnetic (EMI) shielding and grounding structure (not shown) to cover the photo-detector 34. The photo-detector 34 will be influenced by the electromagnetic noise signals in the ambient environment because of its high sensitivity. The EMI shielding and grounding structure can be integrated in the housing 50. The housing 50 for accommodating the detection module 30 can be made of black ABS material to avoid internal light reflection and scattering. Other black machinable materials, such as PLA, PC, PEEK, PPE, and aluminum with black anodized coating are all applicable. The external surface of the housing 50 is coated with metallic paint to insulate the EMI noise on the photo-detector 34. Besides, the material of the housing 50 could be aluminum coated with a dielectric black anodized layer. The black anodized coating not only prevents the short circuit between positive and negative leads of the photo-detector 34, but reduces the internal light scattering inside the optical channel, which is another source of noise signal.

Figure 14A:
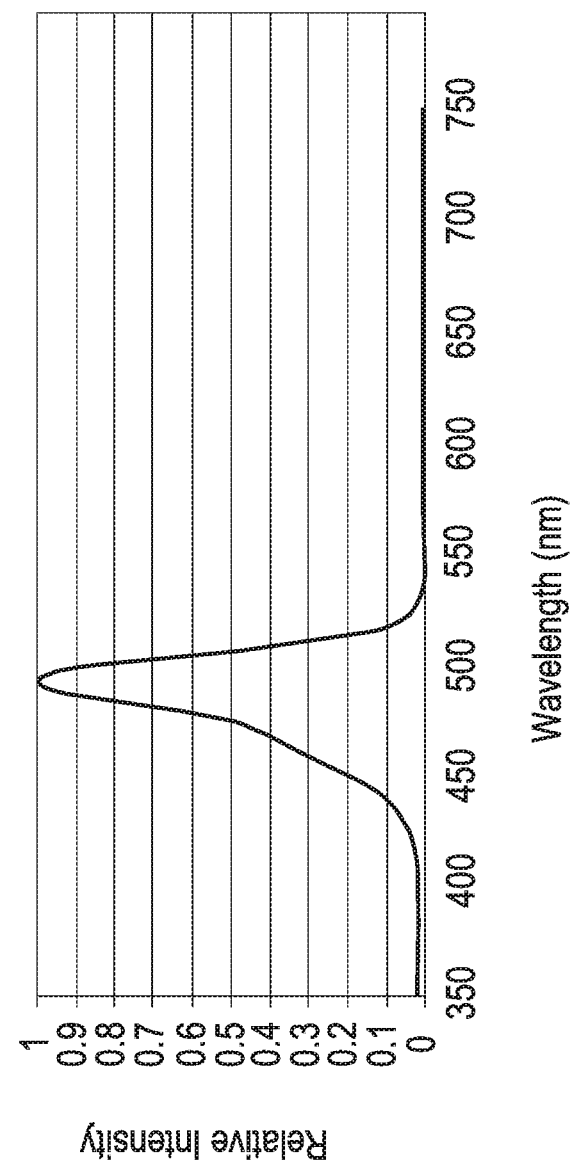
FIG. 14A shows the excitation spectrum of fluorescent dyes FAM.
Figure 14B:
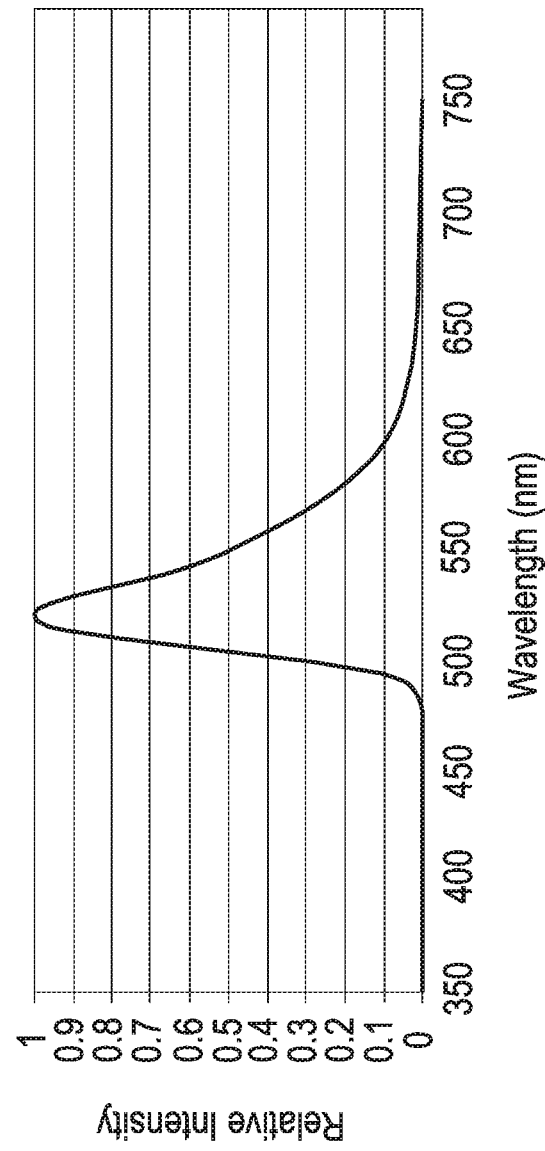
FIG. 14B shows the emission spectrum of fluorescent dyes FAM.
Figure 15A:
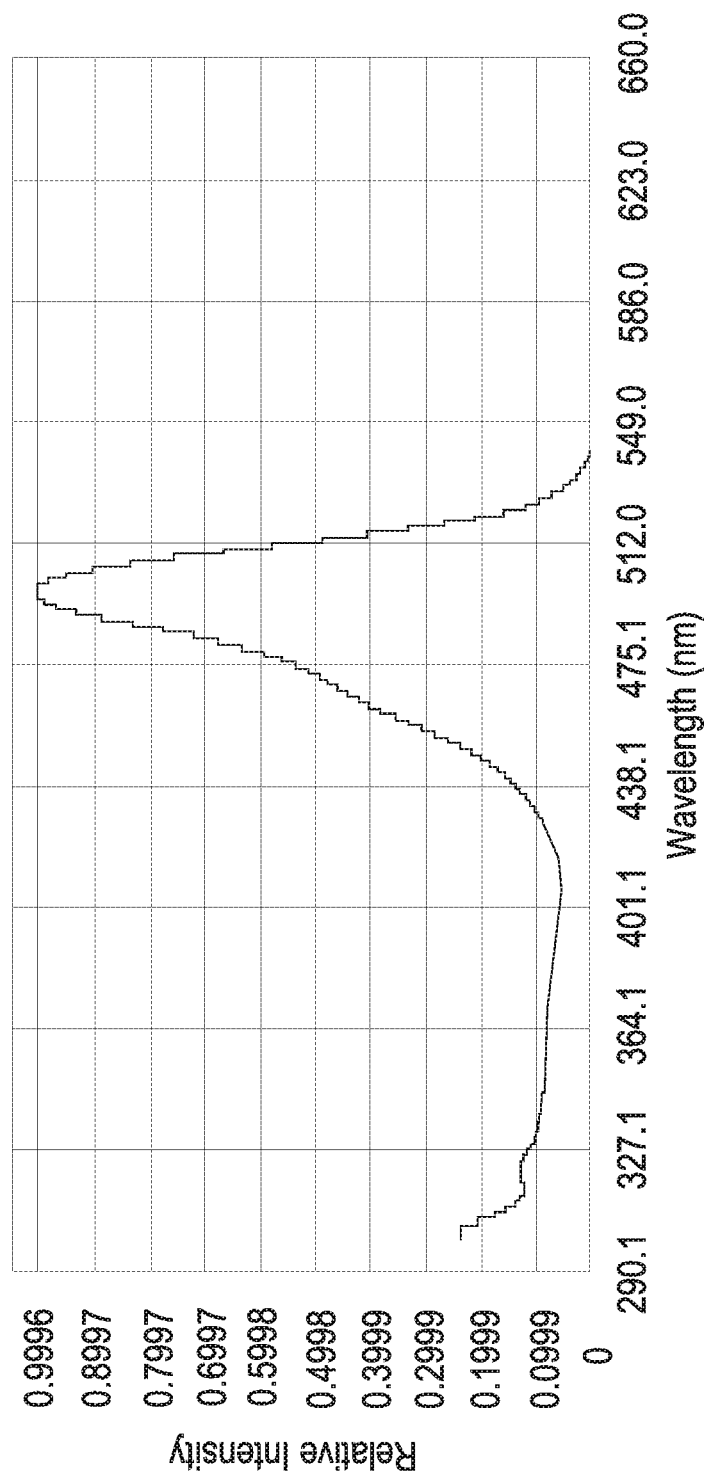
FIG. 15A shows the excitation spectrum of fluorescent dyes FITC.
Figure 15B:
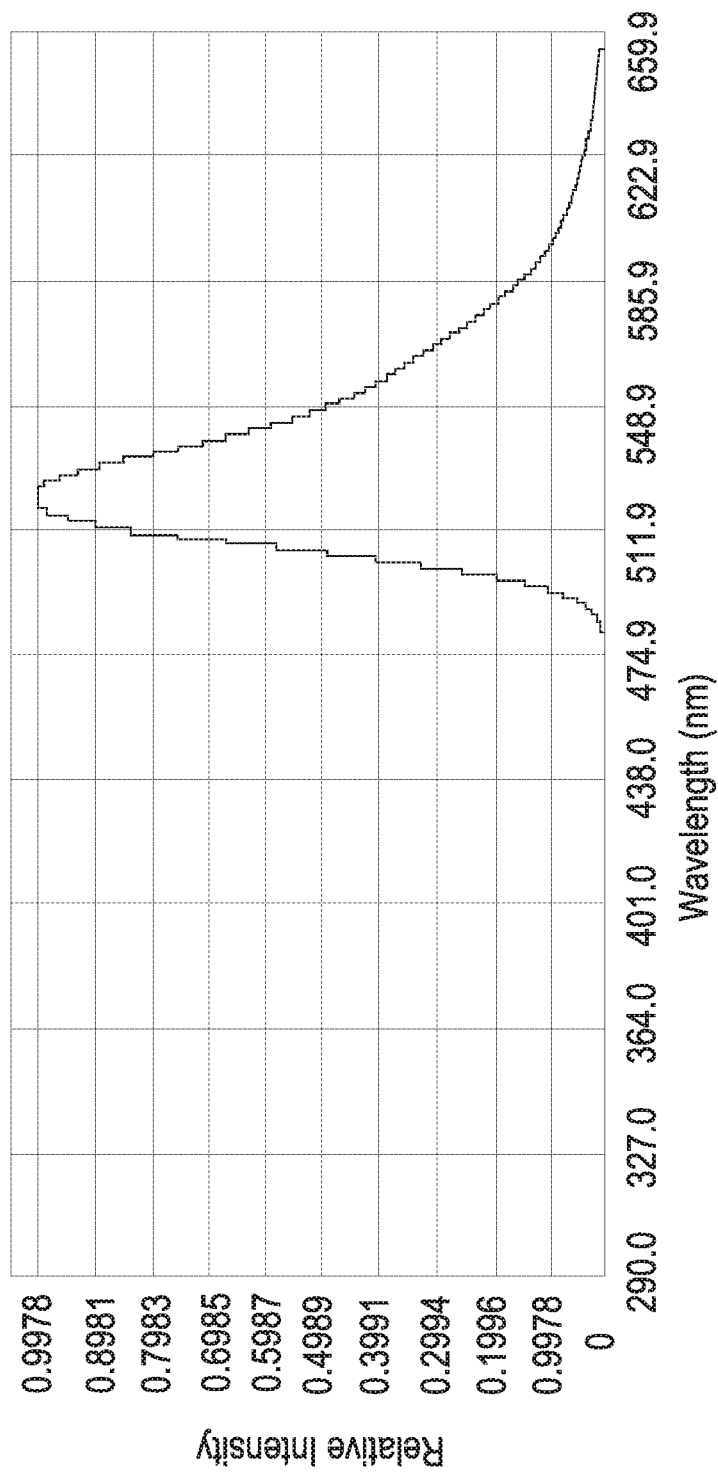
FIG. 15B shows the emission spectrum of fluorescent dyes FITC.

In the embodiment, the fluorescent dyes, FAM or FITC are utilized. The PCR tubes 41 of each channel are filled with the nucleic acids binding with the targeted fluorescent probes. The fluorescent dyes are commercially available fluorescent dyes. FIG. 14A shows the excitation spectrum of the fluorescent dyes FAM, FIG. 14B shows the emission spectrum of the fluorescent dyes FAM, FIG. 15A shows the excitation spectrum of the fluorescent dyes FITC, and FIG. 15B shows the emission spectrum of the fluorescent dyes FITC. Although the preferred embodiment of this invention is described with these fluorescent dyes, the system of this invention is not limited to these types of fluorescent dyes.

It is noted that there are a large number of instruments known in the art that are able to image fluorescence signals. However, one of major problems of such instruments is the noise which comes from the excitation light in comparison with fluorescence light which emitted by the fluorescence probe. To overcome this problem, the present invention arranges the illumination module 10 and the detection module 30 of the fluorescence detection device 1 to be located on two opposite sides of the PCR tube 41 storing of the fluorescent reaction mixtures 40 with the targeted fluorescent probes. The tilted optical axis (i.e. the first optical axis A1) configured the illumination module 10 is defined to have a tilt angle ranged from 4.5 degrees to 9.5 degrees tilting downward from the horizontal optical axis (i.e. the second optical axis A2) of the detection module 30. Consequently, the fluorescence detection device 1 of the present invention is provided with high signal-to-noise ratio.

Figure 16:
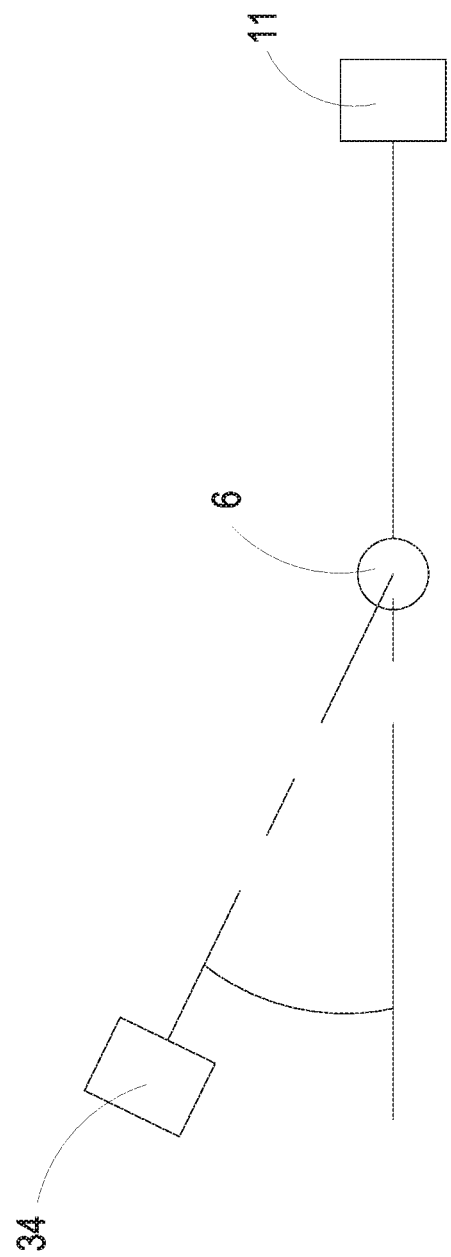
FIG. 16 shows a top view of an experiment setup for analyzing fluorescent emission signal distribution.
Figure 17:
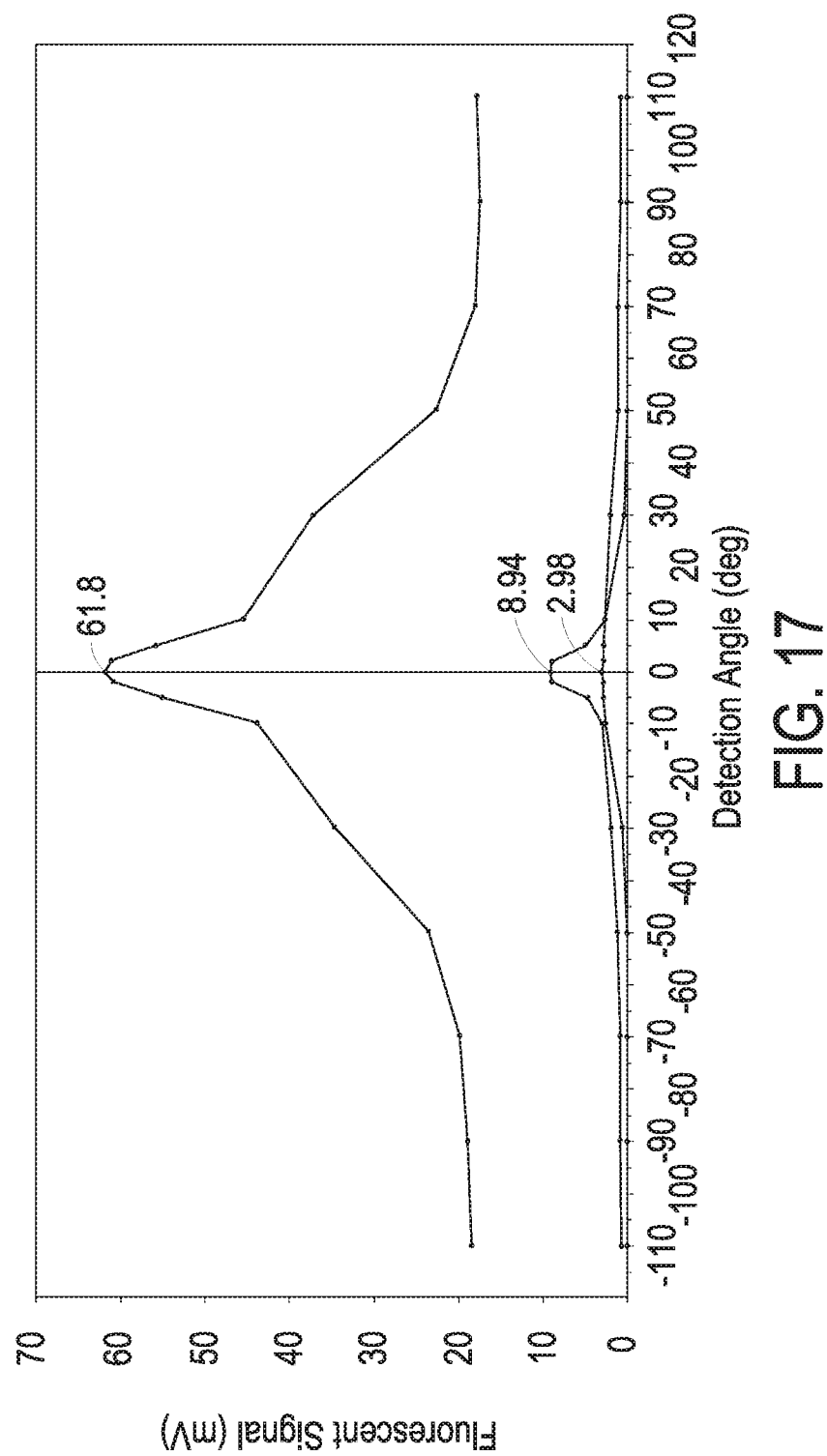
FIG. 17 shows the intensity distribution of emission fluorescent light signal of FITC fluorescent dyes detected in different orientations.
Figure 18:
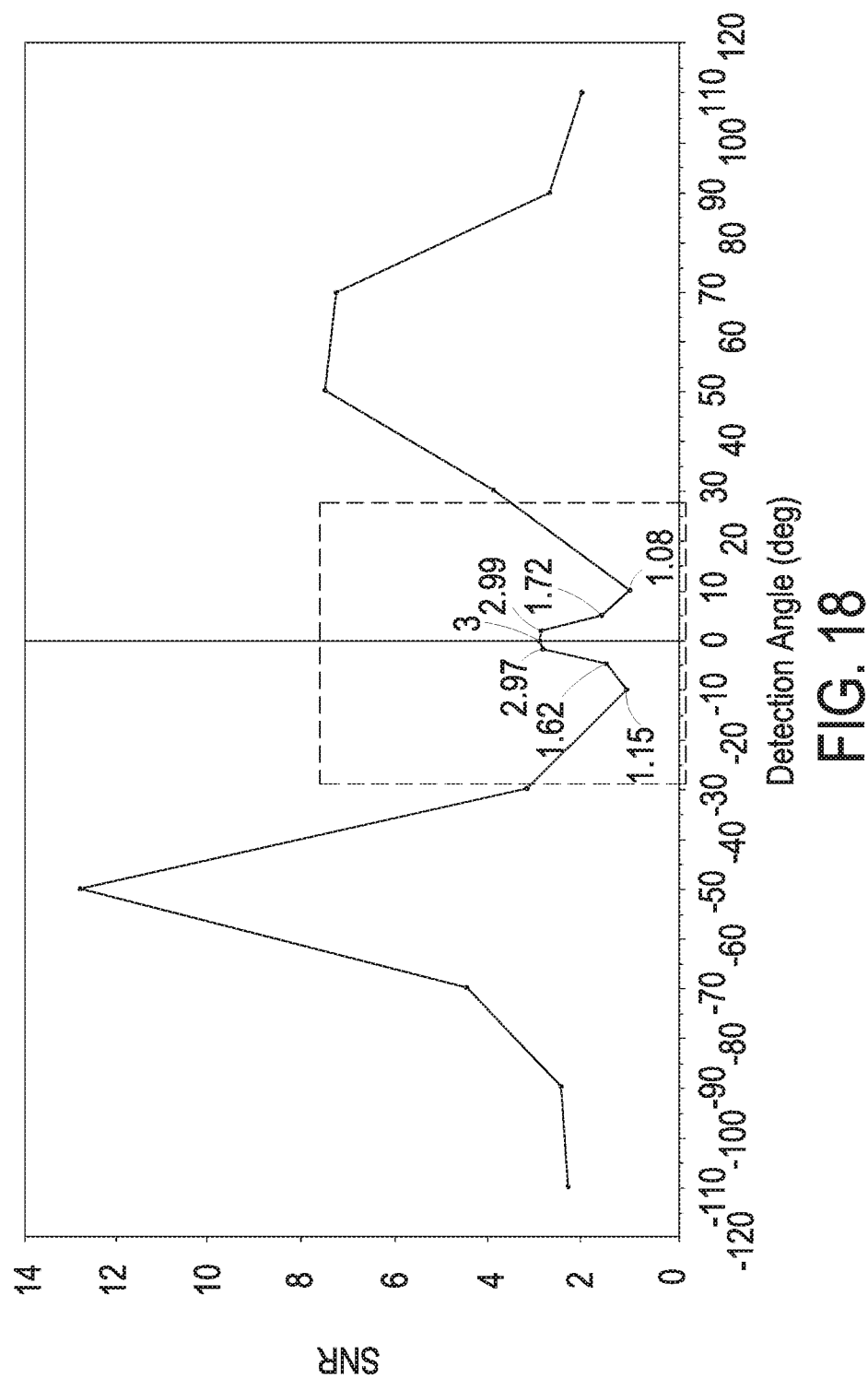
FIG. 18 shows SNR of 20 nM FITC at different detection angles.

FIG. 16 shows a top view of an experiment setup for analyzing fluorescent emission signal distribution. FIG. 17 shows the intensity distribution of emission fluorescent light signal of FITC fluorescent dyes detected in different orientations. FIG. 18 shows SNR of 20 nM FITC at different detection angles.

As shown in FIGS. 16 to 18, the FITC fluorescent dye sample under test is stored in a cylindrical vial 6 and excited by the light source 11, and the photo-detector 34 detects the fluorescent emission light signal in different orientations. The maximum FITC fluorescent emission signal occurs in the forward direction (0 degree). When the photo-detector 34 deviates around ±2.5 degrees, the SNR drops 25% from the peak at 0 degree, which is 3 to 2.17. Although the maximum SNR within the overall deviation angle occurs at 50 degrees, the fluorescent signal detected at 50 degrees is 22.8 mV, which is much weaker than 61.8 mV detected at 0 degree.

According to the experiment results, the properties of the following materials, such as the properties of excitation light source 11, the material properties of PCR tube 41, the properties of PCR reaction mixture 40, the properties of emission light, the optical properties of PCR tube support, and the refractive and scattering behaviors in the tube and liquids need to be considered in the design. So in this invention, the acceptable detection angle between the light source 11 of the illumination module 10 and the position of photo-detector 34 of the detection module 30 fall within a specific angle θ ranged from 4.5 degrees to 9.5 degrees for optimized performance.

Further, according to the article, "Geometrical and Technical Optics" written by N. Lindlein, the propagation of paraxial rays through a tilted refractive planar surface could be expressed in a 3×3 matrix form. The height and angle of output paraxial ray is y' and α', where the matrix $M_S$ is the propagation matrix of the optical system.

$$\begin{bmatrix} \gamma' \\ \varphi' \\ 1 \end{bmatrix} = M_s * \begin{bmatrix} \gamma \\ \varphi \\ 1 \end{bmatrix}$$

Transfer matrix describes the variation of paraxial ray height propagating in a distance d of the same medium. It could be expressed as $$T = \begin{bmatrix} 1 & d & 0 \\ 0 & 1 & 0 \\ 0 & 0 & 1 \end{bmatrix}$$

Refraction matrix describes the deviation of paraxial ray angle propagating from medium 1 to medium 2. The refractive index of medium 1 is n, and the refractive index of medium 2 is n'. α is the angle of planar surface.

$$R = \begin{bmatrix} 1 & 0 & 0 \\ 0 & \dfrac{n}{n'} & \dfrac{n'-n}{n'}\alpha \\ 0 & 0 & 1 \end{bmatrix}$$

Figure 19:
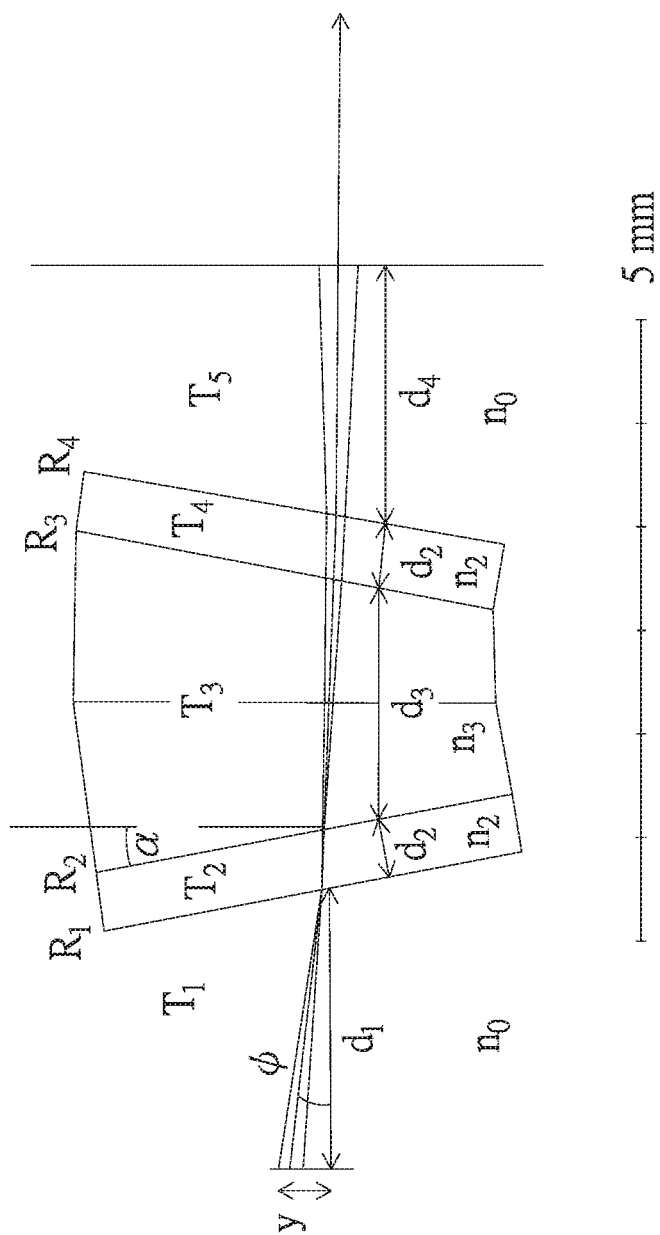
FIG. 19 shows a paraxial ray trace diagram similar to the optical system of the fluorescence detection device.

FIG. 19 shows a paraxial ray trace diagram similar to the optical system of the fluorescence detection device. The propagation matrix of the system of FIG. 19 is shown below:

$$M_S = T_5 * R_4 * T_4 * R_3 * T_3 * R_2 * T_2 * R_1 * T_1$$

Therefore, the relationship of height and angle of paraxial output and input beam are simplified below:

$$\varphi' = \varphi + 2*(n_3 - n_0)*\alpha/n_0$$

$$y'=y+(d_1+2n_0*d_2/n_2+n_0*d_3/n_3+d_4)*\varphi+2*(n_3-n_0)$$
$$*\alpha*d_2/n_2+(n_3-n_0)*\alpha*d_3/n_3+2*(n_3-n_0)*\alpha*d_4/n_0$$

Accordingly, the relationship of angle of input and output beam of the fluorescence detection device 1 of the present invention can be determined as the result in Table 1. In Table 1, the output angle of excitation beam varies within 0±2.5 degree when the input light source is position 7±2.5 degree for optimized performance.

TABLE 1

| $\varphi$ (deg) | 4.5 | 7 | 9.5 |
|---|---|---|---|
| $\varphi'$ (deg) | 2.510 | 0.010 | −2.490 |

Figure 20:
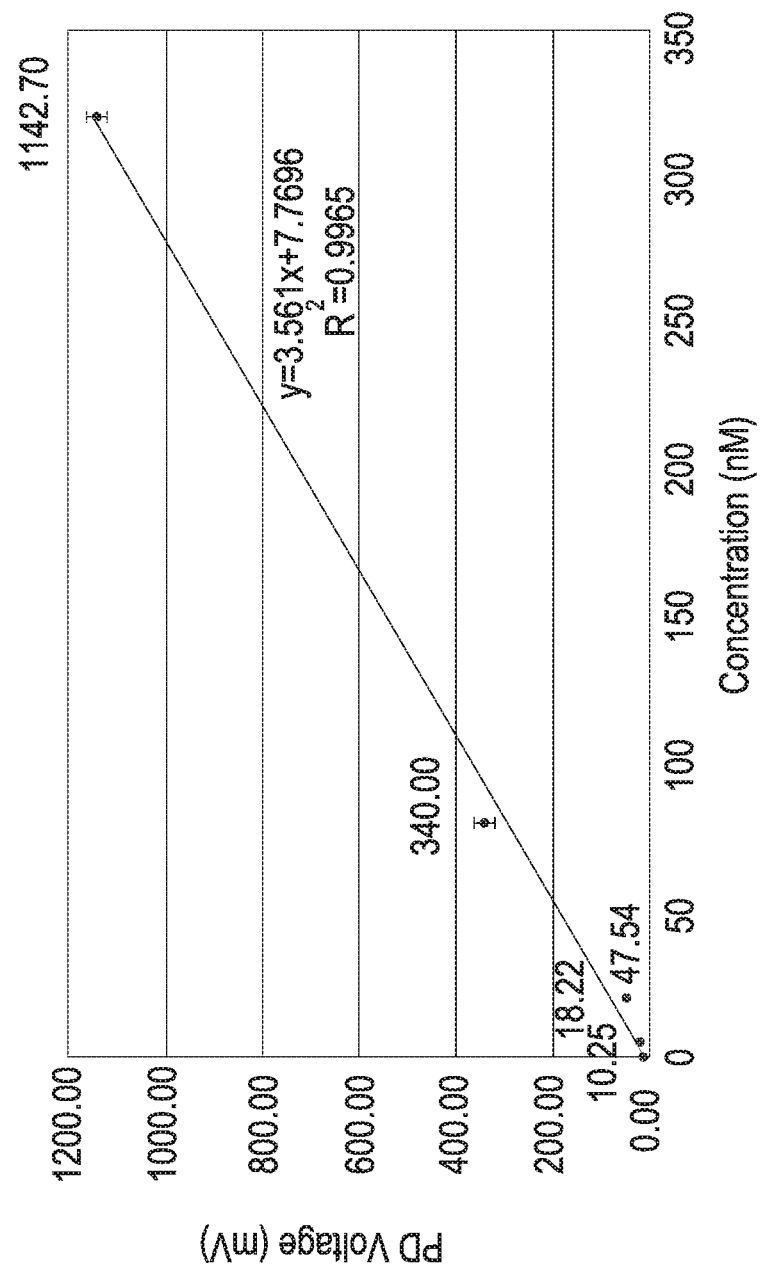
FIG. 20 shows the intensity distribution of FITC of different concentrations when the input light source is positioned with a tilt angle of 7 degrees.

FIG. 20 shows the intensity distribution of FITC of different concentrations when the input light source is positioned with a tilt angle of 7 degrees. Table 2 further shows the related SNR of detected intensity at different concentrations. As shown in FIG. 20 and Table 2, while the concentration is increased, the intensity of detected signal and SNR are increased. In Table 2, it further shows that the fluorescence detection device 1 with the input light source 11 tilted at 7 degrees can provide promising performance whose signal to noise ratio (SNR) could be up to 111.

TABLE 2

| Concentration (nM) | PD Voltage (mV) | SNR |
|---|---|---|
| 0 | 10.25 | |
| 20 | 340 | 4.64 |
| 320 | 1142.7 | 111.46 |

In conclusion, the present invention provides the fluorescence detection device integrating with heating module for thermal cycling in PCR application. The well-designed optical structure miniaturizes the size and reduces the cost of the illumination module and the detection module, but still provides promising performance whose signal to noise ratio (SNR) could be up to 111. The overall dimension of the system is about 80 mm×35 mm×20 mm. The components and structure of the fluorescence detection device contributes the compactness of this optical system. The arrangement of the illumination module provides the most efficient light source for exciting the targeted fluorescent probe in the PCR fluorescent reaction mixture. The sandwich-type arrangement of the condensing optics and the imaging optics ensures the miniaturization of this optical system because the spacing between the condensing optics, the emission filter, and the imaging optics are well designed. The invention prevents the interference of noises due to scattering and reflection of the light source.

Further, the design of optical path is transmissive, and according to the experimental result, the incident angle of the light source configured on the optical axis is defined as a specific angle ranged from 4.5 degrees to 9.5 degrees tilting downward from the horizontal axis to achieve maximum optical intensity on the application of low fluorescent signal detection system. From experiment and simulation result, fluorescent sample is stored in a cylindrical container, and the peak intensity of fluorescent emission signal occurred at zero degree, which is also called forward scattering. For matching the conical shape of the commercial PCR tube, the angle between light source and photo-detector falling ranged from 4.5 degrees to 9.5 degrees is the optimum conditions. The signal-to-noise ratio (SNR) is also within the best performance range. The optimal angle of incidence could dramatically reduce the internal scattering and multiple reflections occurred in the PCR mixture. Besides, the optical apertures created at the front and rear sides of the heating module determine the sufficient light signal for excitation and emission.

In addition, the design and arrangement of the first and second single band pass filters as excitation and emission filters, respectively, help to achieve the compactness of qPCR system. Besides, the filter sets reduce the interference of noise signal, and allow excitation light beam and emission fluorescent light to be fully utilized, so that the fluorescence detection device is able to provide high signal-to-noise ratio (SNR).

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A fluorescence detection device comprising:
an illumination module including at least one light source and at least one first filter, the light source providing a broadband illumination and being configured with the first filter to pass a first light beam at a first particular bandwidth along a first optical axis for exciting a targeted fluorescent probe of a fluorescent reaction mixture stored in a tube and generating a fluorescent light; and
a detection module including at least one second filter and at least one photo-detector, the second filter being configured for receiving the fluorescent light and passes a second light beam at a second particular bandwidth along a second optical axis, the photo-detector for receiving the second light beam at the second particular bandwidth and converting the second light beam at the second particular bandwidth to an electrical signal;
wherein the first optical axis is tilted from the second optical axis at an angle ranged from 4.5 degrees to 9.5 degrees.

2. The fluorescence detection device according to claim 1, wherein the light source is one selected from a group consisted of a single color LED, a laser diode, a mercury lamp and a halogen light bulb.

3. The fluorescence detection device according to claim 1, wherein the first filter and the second filter are single band pass filters.

4. The fluorescence detection device according to claim 1, wherein the first filter and the second filter are an excitation filter and an emission filter respectively.

5. The fluorescence detection device according to claim 1 further comprising a heating module disposed between the illumination module and the detecting module, wherein the heating module comprises at least one heating chamber adapted for accommodating the tube having the fluorescent reaction mixture and the targeted fluorescent probe.

6. The fluorescence detection device according to claim 5, wherein the heating module further comprises a heater connected with the heating chamber.

7. The fluorescence detection device according to claim 6, wherein the heater is a thermoelectric cooling heater for thermal cycling control.

8. The fluorescence detection device according to claim 5, wherein the heating module further comprises at least one first optical aperture and at least one second optical aperture, the first optical aperture is located at the first optical axis, the second optical aperture is located at the second optical axis, and the first optical aperture is communicated with the second optical aperture through the heating chamber.

9. The fluorescence detection device according to claim 8, wherein the diameter of the first optical aperture is ranged from 1.8 mm to 2.2 mm, and the diameter of the second optical aperture is ranged from 1.5 mm to 2.5 mm.

10. The fluorescence detection device according to claim 8, wherein the illumination module further comprises at least one pine hole located between the first filter and the first optical aperture and located at the first optical axis, and the diameter of the pin hole is ranged from 1.3 mm to 1.8 mm.

11. The fluorescence detection device according to claim 9, wherein the second optical aperture of the heating module and the detection module are configured together to form a divergent half angle ranged from 18 degrees to 22 degrees.

12. The fluorescence detection device according to claim 5, wherein the detection module further comprises at least one condensing optic disposed between the heating chamber and the second filter.

13. The fluorescence detection device according to claim 12, wherein the condensing optic includes a plano surface facing to the second optical aperture and a convex surface facing to the second filter.

14. The fluorescence detection device according to claim 1, wherein the detection module further comprises at least one imaging optic disposed between the second filter and the photo-detector.

15. The fluorescence detection device according to claim 14, wherein the imaging optic includes a plano surface facing to the photo-detector and a convex surface facing to the second filter.

16. The fluorescence detection device according to claim 1, wherein the detection module further comprises at least two optics symmetrically disposed in two opposite sides of the second filter with a same distance, wherein each optic includes a convex surface faces toward the second filter.

17. The fluorescence detection device according to claim 1, comprising a housing, wherein the illumination module and the detection module are constructed together on the housing.

18. The fluorescence detection device according to claim 1, wherein the detection module further comprises a photo-diode amplifier connected with the photo-detector.

19. The fluorescence detection device according to claim 1, wherein the detection module further comprises an electromagnetic shielding and grounding structure covering the photo-detector.

20. The fluorescence detection device according to claim 1, wherein the photo-detector is one selected from a group consisted of a silicon photodiode, a photomultiplier tube, a charged-couple device, and a complementary metal-oxide semiconductor.

* * * * *